United States Patent [19]

Kubo et al.

[11] Patent Number: 4,731,493

[45] Date of Patent: Mar. 15, 1988

[54] PROCESS FOR PRODUCING CONDENSED BROMOACENAPHTHYLENE

[75] Inventors: Masashige Kubo; Mitsuaki Yoshimitsu; Yukihiro Tsutsumi, all of Yamaguchi, Japan

[73] Assignee: Toyo Soda Manufacturing Co., Ltd., Shinnanyo, Japan

[21] Appl. No.: 819,269

[22] Filed: Jan. 16, 1986

Related U.S. Application Data

[63] Continuation of Ser. No. 537,581, Sep. 30, 1983, abandoned.

[30] Foreign Application Priority Data

Sep. 30, 1982 [JP] Japan ................... 57-169835
Oct. 1, 1982 [JP] Japan ................... 57-171015

[51] Int. Cl.$^4$ ................. C07C 17/26; C07C 17/34; C07C 17/02
[52] U.S. Cl. ............................ 570/204; 570/183
[58] Field of Search ............... 570/204, 200, 197, 198, 570/206, 211; 526/75, 78, 280; 525/330.7, 333.4

[56] References Cited

U.S. PATENT DOCUMENTS

| | | | |
|---|---|---|---|
| 2,768,147 | 10/1956 | Meis et al. | 526/280 |
| 3,448,156 | 6/1969 | Taussig et al. | 570/197 |
| 3,647,895 | 3/1972 | Fruhwirth et al. | 570/211 |
| 3,845,146 | 10/1974 | Moore et al. | 570/206 |
| 4,373,046 | 2/1983 | Hagiwara et al. | 526/280 |
| 4,394,484 | 7/1983 | Jenkner et al. | 526/75 |

FOREIGN PATENT DOCUMENTS

| | | | |
|---|---|---|---|
| 2950877 | 6/1981 | Fed. Rep. of Germany | 570/206 |
| 106227 | 8/1980 | Japan | 526/280 |
| 139630 | 7/1985 | Japan | 570/204 |
| 986634 | 3/1965 | United Kingdom | 570/200 |
| 2131017 | 6/1984 | United Kingdom | 570/204 |
| 358308 | 1/1973 | U.S.S.R. | 570/204 |

OTHER PUBLICATIONS

Y. Morita et al, "Synthesis of Brominates Acenaphthylenes and Their Flame Retardant Effects on Ethylene Propylene-Diene Terpolymer, Journal of Applied Polymer Science, vol. 27, 3329-3339 (1982).

*Primary Examiner*—J. E. Evans
*Attorney, Agent, or Firm*—Oblon, Fisher, Spivak, McClelland & Maier

[57] ABSTRACT

Process for producing condensed bromoacenaphthylene comprising:

(A) a step of brominating and condensating acenaphthene with bromine in a halogenated hydrocarbon solvent in the presence of a Lewis acid catalyst;

(B) a step of removing the Lewis acid catalyst and then continuing the bromination with bromine with an added radical initiator; and (C) a step of carrying out dehydrobromination reaction.

In a modified process, the bromination is effected in a halogenated hydrocarbon solvent at a temperature not lower than 60° C. using bromine at least 3 times as much in moles as acenaphthene in the presence of an iron catalyst.

Further, the condensed bromoacenaphthylene is purified by bringing it into contact with an adsorbent in an organic solvent.

19 Claims, No Drawings

PROCESS FOR PRODUCING CONDENSED BROMOACENAPHTHYLENE

This is a continuation of application Ser. No. 537,581, filed Sept. 30, 1983, now abandoned.

BACKGROUND OF THE INVENTION

1. Field of the Invention

The present invention relates to a process of production and purification of condensed bromoacenaphthylene.

2. Description of the Prior Art

In recent years for precautions against fire, it has been a widely adopted practice that various inflammable resins, such as polyethylene, polypropylene and ethylenepropylene rubbers are made non-flammable and for this purpose a method is known, which comprises adding various flame retarders to the resins. Further, it has been an extreme necessity that electric cables and various instruments used in nuclear or breeder reactors and ionization radiation generators etc. are non-flammable for security and safety. Therefore, various materials employed for the cables and instruments, such as insulating coating materials and many kinds of resin compositions, are required to be radiation resisting as well as non-flammable.

Condensed bromoacenaphthylene is a compound having excellent non-flammable and radiation resisting properties. The double bond in the molecule of the compound facilitates grafting to resins by treatment for radical generation. Also by virtue of its nature as a condensate, the compound has excellent miscibility with resins, because it does not breed on the surface of resins or it is not lost by volatilization for a long run. Thus the compound is capable of maintaining non-flammable and radiation resisting properties for a long period (Japanese Laid-Open Patent Application No. Sho 56-122862).

For the production of condensed bromoacenaphthylene, two processes have been proposed; one proposal uses iron (III) chloride as catalyst and bromination is carried out with bromine 6 times as much as acenaphthene at a temperature between 20° and 30° C. (Morita and Hagiwara: The 30th High Molecular Conference, G3A14, Tokyo(1981)), and the other proposal treats brominated acenaphthene in which bromine has been introduced at the arylic and benzylic positions in the presence of a catalyst for the synthesis (Japanese Laid-Open Patent Application No. Sho 56-122862).

The former process, however, has been found to be accompanied with a lower yield, because a significant amount of polybrominated monomers is produced as by-product. According to the latter proposal, which proposes condensation of, for example, 1,2,3,5-tetrabromoacenaphthene in the presence of a catalyst, the carbon atom at the benzylic position at which a bromine atom is attached is so highly reactive as readily to give rise to the Friedel-Crafts type of alkylation reaction in the presence of a Lewis acid catalyst, so that one cannot control the degree of condensation. As a result, bromine atoms are significantly lost at the benzylic positions and subsequent dehydrobromination reaction can produce only a reduced number of double bonds than otherwise. Further, the starting material, brominated acenaphthene in which bromine has been introduced at the arylic and the benzylic positions, can be produced in a troublesome and hard way with only a low yield, when commercially available acenaphthene is used as the first starting material.

Meanwhile, condensed bromoacenaphthylene, which has been produced from acenaphthene by bromination and condensation followed by dehydrobromination reactions, usually contains minute amounts of derivatives as impurities which are objectionable in practical treatment and usage.

The impurities are absorbed on the surface, and contained in the bulk of the condensate and they cannot be easily removed therefrom by the ordinary filtration, washing and reprecipitation. This fact caused practical drawbacks often encountered in operations. For example, the condensed bromoacenaphthylene adheres onto a roll surface when kneaded with a resin using a roller and, in the case of a shaped composition, the condensed bromoacenaphthylene breeds like pollen on the surface of the resin. Further its adverse effects are observed on tensile strength, elongation, and water-proofness at high temperatures.

With these problems in mind, the present inventors intensively investigated for a process for production and purification of condensed bromoacenaphthylene from acenaphthene as starting material, and the following facts have been found.

(1) Bromination of acenaphthene carried out at a temperature between 5° and 55° C. using a Lewis acid catalyst produces brominated acenaphthene and condensate thereof which are brominated only at the arylic position, and not at the benzylic position.

(2) Bromination reaction of acenaphthene with elemental bromine in the presence of a radical initiator produces a compound which is brominated at the benzylic position. Then if the bromination reaction is continued with added bromine and a Lewis acid catalyst for accelerating bromination at the arylic position, a compound with an extremely high degree of condensation is obtained, but a benzylically brominated compound is difficult to obtain.

Further investigation revealed that condensed bromoacenaphthylene can be produced by following treatments:

(A) a step of treatment in which acenaphthene is brominated with bromine and condensed in a halogenated hydrocarbon in the presence of a Lewis acid catalyst;

(B) a step of treatment in which the Lewis acid catalyst is removed and bromination reaction with bromine was continued with a radical initiator added; and (C) a step of treatment in which the dehydrobromination reaction is carried out.

It has been further found that a condensate which is brominated not only at the arylic position but also at the benzylic position can be produced, though in a small amount, only when bromination of acenaphthene is carried out with bromine at least 3 times as much in moles as acenaphthene at a temperature between 5° and 55° C. using iron catalysts as the Lewis acid catalysts.

Therefore, more investigation has been made to reveal a surprising fact, that when bromination and condensation of acenaphthene is carried out in a halogenated hydrocarbon solvent at a temperature of 60° C. or higher in the presence of iron catalyst using bromine at least 3 times as much in moles as acenaphthene, an acenaphthene condensate which is brominated at the benzylic position is obtained with a satisfactorily high yield.

Meanwhile, the condensed bromoacenaphthylene which is produced by the bromination, condensation and dehydrobromination reactions of acenaphthene can be purified by dissolving the condensate in an organic solvent and bringing it in contact with an appropriate amount of an inorganic oxide, an alkaline earth metal salt or amorphous carbon, thus selectively removing by adsorption of those minute impurities which cause the adherence on rollers and the breeding, and hence assuring successful production of a resin composition from the condensed bromoacenaphthylene with improved physical properties.

SUMMARY OF THE INVENTION

The present invention is summarized as below.

(1) Process for producing condensed bromoacenaphtylene having the general formulae [I] or [II] as elementary unit

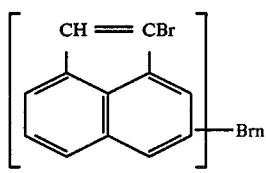

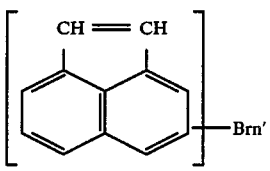

(where n and n' are integers ranging from 1 to 5), comprising
  (A) a step of brominating and condensating acenaphthene with bromine in a halogenated hydrocarbon solvent in the presence of a Lewis acid catalyst;
  (B) a step of removing the Lewis acid catalyst and then continuing the bromination with bromine with an added radical initiator; and
  (C) a step of carrying out dehydrobromination reaction (hereinafter called the basic process).

(2) Process for producing condensed bromoacenaphthylene having the general formulae [I] or [II] as elementary unit

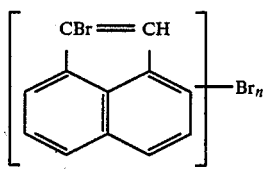

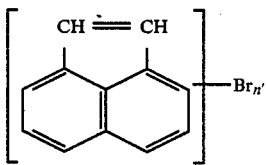

(where n and n' are integers ranging from 1 to 5) by the bromination and condensation reactions of acenaphthene followed by dehydrobromination reaction, comprising brominating and condensating acenaphthene in a halogenated hydrocarbon solvent at a temperature not lower than 60° C. using bromine at least 3 times as much in moles as acenaphthene in the presence of an iron catalyst (hereinafter called the modified process).

(3) And, process for purifying condensed bromoacenaphthylene prepared by bromination and condensation reactions of acenaphthene followed by dehydrobromination reaction, comprising bringing the condensed bromoacenaphthylene into contact with an inorganic oxide, an alkaline earth metal salt or amorphous carbon as adsorbent in an organic solvent (hereinafter called the purification process).

DETAILED DESCRIPTION OF THE INVENTION

Condensed bromoacenaphthylene produced by the process of this invention is a compound which contains at least one bromine atom per aromatic ring and is prepared formally by the condensation of brominated acenaphthylene, followed by the dehydrobromination reaction, into a polymer having the degree of condensation not less than 2.

In this compound, the bonding is made intermolecularly between a benzylic carbon of one acenaphthylene and an arylic carbon of another acenaphthylene. The benzylic and the arylic positions referred to in this invention are the side chain and the naphthalene nucleus of acenaphthene ring, respectively. The bonding can be shown, for example, as below:

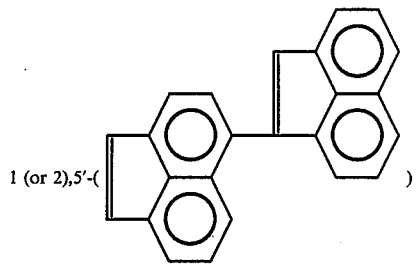

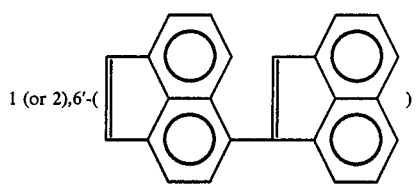

Other bondings such as 1(or 2),3'-, 1(or 2),4'-, 1(or 2),7' and 1(or 2),8'- are also possible. Polymers with the degree of condensation of 3 or larger have been formed by these bondings.

Condensates referred to in this invention are those having the degree of condensation not larger than 10 and good miscibility with resins.

According to the basic process of the present invention, the arylic bromination and condensation occur simultaneously in the bromination reaction in the first stage, and the benzylic bromination takes place in the second stage. Thus, the balance between bromination and condensation is well controlled and the quantitative generation of double bonds is also effected.

The basic process of this invention may be explained using following reaction formulae:

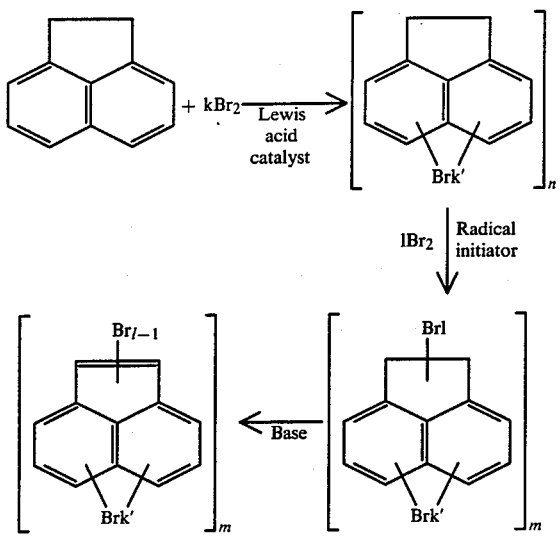

(where k, k' are integers between 1 and 5, l is an integer 1 or 2, and m is an integer between 1 and 10).

The basic process of this invention is described in details for each step of process.

Step (A):

Acenaphthene is dissolved in a halogenated hydrocarbon solvent and is submitted to bromination with bromine and simultaneously to condensation in the presence of a Lewis acid catalyst.

The halogenated hydrocarbon solvents to be used in this step are those which are inert to the reaction, and they include, for example, carbon tetrachloride, chloroform, methylenechloride, ethylenedichloride, ethylenedibromide and chlorobenzene. There is no particular restriction on the amount of the solvent.

As for the Lewis acid used as catalyst, metal halogenides are preferred and iron catalysts, such as iron (III) chloride and aluminum catalysts, such as aluminum chloride, are usually employed. The amount of catalyst used for unit mole of acenaphthene is 0.1 to 50 moles, preferably 1 to 20 moles.

The amount of bromine used in this step is usually 1 to 6 moles, preferably 2 to 5 moles per unit mole of acenaphthene.

The bromination reaction is preferably carried out at a temperature between 10° and 60° C.

Step (B):

The reaction mixture solution resulting in step (A) is treated to remove the catalyst contained, for example, by washing with water, and a radical initiator is added, and then bromination reaction is started with addition of bromine.

The condensed bromoacenaphthene produced in step (A) contains almost no benzylic substituted bromide which, however, can be produced quantitatively in this step.

The radical initiators to be used in this step are preferably decomposable thermally to form a radical, and peroxides and azo compounds that are usuable in a temperature ranging from 30° to 100° C. are generally preferred. They include benzoyl peroxide, acethyl peroxide, lauroyl peroxide, and azo-bis(isobutylonitrile).

Regarding the amount of bromine used in this step, one to two moles of bromine are used for unit mole of acenaphthene. Bromination reaction is usually carried out at 30° to 100° C. However, a higher temperature is preferred, because a higher selectivity is obtained with respect to the benzylic bromination in addition to accelerated reaction, and almost no condensation takes place in this reaction.

Step (C):

The condensed bromoacenaphthene produced in step (B) is dissolved in an inert solvent and, with addition of a base, dehydrobromination is carried out.

The reaction solvent is selected among halogenated hydrocarbons, aliphatic and aromatic hydrocarbons, and ethers. They include, for example, carbon tetrachloride, ethylenedichloride, hexane, benzene, toluene and tetrahydrofurane, and the base is selected among compounds conventionally used for ordinary dehydrobromination, such as methanolic solutions of potassium hydroxide and sodium hydroxide.

The reaction is carried out usually at 30° to 100° C., but a higher temperature is preferred because the reaction can be accelerated and may progress quantitatively.

According to the second aspect of this invention, it is possible to balance the ionic reaction, which is involved in the arylic bromination and condensation, with the radical reaction of the benzylic bromination, so that it is possible to obtain an acenaphthene condensate in which bromination takes place at both of the arylic and benzylic positions. Further, an insoluble by-product which contains substituted bromine atoms at the aryl-site is produced in a much smaller proportion, hence a higher yield of desired product can be assured.

The modified process of the present invention will be described in more details. Halogenated hydrocarbons, such as carbon tetrachloride, chloroform, dichloroethylene, dibromoethylene, chlorobenzene, bromobenzene and dichlorobenzene are used for the solvent. There is no particular restriction on the amount of solvent.

The iron catalyst to be used in this case may be those usually used for halogenation of aromatic hydrocarbons. They include, for example, halogenides of iron such as iron (II) chloride and iron (III) bromide, salts of iron such as iron (III) phosphate, iron oxide such as iron (III) oxide and iron powder. The amount of these catalyst to be added may be selected from 0.001 to 0.5 mole per unit mole of acenaphthene, but preferably between 0.01 and 0.2 mole on considering the reaction efficiency.

The amount of bromine used in this case should be not less than 3 moles, preferably not less than 4 moles, per unit mole of acenaphthene. With amounts of bromine less than 3 moles, almost all of the benzylic substituted bromide is consumed in the condensation reaction and therefore the aimed compound, condensed bromoacenaphthylene, cannot be produced. On the other hand, if the bromine exceeds 6 moles, expenses such as for recovery of unreacted bromine is significant, though there is no trouble to the desired reaction. Therefore, the amount of bromine is preferably less than 6 moles.

The temperature of reaction should be 60° C. or higher, preferably between 70° C. and 170° C. At temperatures below 60° C., ionic reactions prevail over radical reactions and polybrominated acenaphthene monomers are produced in a larger amount in the form of insoluble product. When the temperature is not lower than 60° C., a good balance is maintained between the radical and the ionic reactions and the insoluble by-product is formed little, hence the condensed bromoacenaphthylene aimed at can be obtained with a high yield.

The reaction is usually carried out under a normal pressure in a halogenated hydrocarbon solvent containing acenaphthene and iron catalyst to which bromine is added dropwise. The same reaction, however, can occur under an increased pressure.

The condensed bromoacenaphthylene thus obtained is then dissolved in an inert solvent and a base, such as a methanolic solution of potassium hydroxide is added to induce dehydrobromination reaction. Thus condensed bromoacenaphthylene can be produced.

According to the process of the present invention, an economical process for producing condensed bromoacenaphthylene has been realized, in which commercially available materials are used as raw stuffs and an intermediate of condensed bromoacenaphthylene can be prepared in a simple procedure and with a high yield.

Moreover, the benzylic C—C double bonds are formed quantitatively in the condensed bromoacenaphthylene of this invention, which results in a high effeciency in graft formation with resins as well as high radiation resistivity and non-inflammability.

In the next place, the purification process of this invention is explained relating to the purification of condensed bromoacenaphthylene.

The purification process of this invention provides a part in the process of producing a condensed bromoacenaphthylene. Thus, this invention provides a process for purifying the condensed bromoacenaphthylene produced by bromination and condensation of acenaphthene followed by dehydrobromination reactions, characterized by bringing the condensate into contact with an adsorbent in an organic solvent.

Any organic solvents that dissolve condensed bromoacenaphthylene can be used in the purifying process according to this invention. They include carbon tetrachloride, chloroform, ethylenedibromide, chlorobenzene, benzene, toluene, tetrahydrofurane, acetone and carbon disulfide. Further, the amount of solvent is not particularly restricted so far as it is sufficient enough to completely and homogeneously dissolve the condensed bromoacenaphthylene.

Among adsorbents, inorganic oxide, alkaline earth metal salts, amorphous carbon and any mixture of these substances are suited to use in the process of this invention.

As inorganic oxides, oxides of IIIb and IVb group metals are selected, including alumina, silica gel, silica-alumina, diatom earth and zeolite. Among them, alumina is particularly remarkable in the purification efficiency.

Among alkaline earth metal salts, carbonates, phosphates, and silicates are recommended, for example, such as calcium carbonate, calcium phosphate, magnesium carbonate, magnesium silicate.

Examples of amorphous carbon are active charcoal, charcoal, coke, carbon black. Particularly desirable is active charcoal, regardless of being granular or powdery.

These adsorbents are used in an amount of 0.01 to 1000 parts by weight per 100 parts by weight of condensed bromoacenaphthylene. The amount may be selected arbitrarily within the specified range, but 0.05 to 100 parts by weight are preferred from the practical point of view.

The adsorbents may be brought into contact with a solution of the condensed bromoacenaphthylene in a usual manner. For example, the solution may be introduced into a column packed with an adsorbent, or both are mixed or shaked in a vessel. The temperature at which the contact is made little affects the efficiency of adsorption, but usually a temperature between 0° and 70° C. is selected because the condensed bromoacenaphthylene loses stability at high temperatures.

After treated with these adsorbents, pure condensed bromoacenaphthylene can be recovered in a usual manner from the solution. For example, the solution is concentrated and cooled to obtain separated crystals, or the solution is poured into a poorer solvent for deposition.

As is evident from the above description, a condensed bromoacenaphthylene produced by bromination and condensation of acenaphthene followed by dehydrobromination reactions can be made free from impurities by the process of this invention. The process is simple and the impurities are removed selectively and easily. The condensed bromoacenaphthylene thus purified does not adhere onto a roller when kneaded with a resin on rollers, suppresses breeding from a shaped composition, and shaped compositions from the condensate are remarkable improved in their mechanical properties.

DESCRIPTION OF PREFERRED EMBODIMENTS

The present invention will be better understood from the following description of preferred embodiments. However, the present invention should not be restricted to these embodiments in any sense.

EXAMPLE 1

A mixture of 77 g of acenaphthene and 8.1 g of iron (III) chloride in 690 ml of carbon tetrachloride was warmed at 60° C. To this solution, 240 g of bromine dissolved in 60 ml of carbon tetrachloride was dropwise added in 2 hours. Reaction was continued until the color of bromine disappeared and the solution was washed with 300 ml of 1N aqueous hydrochloric acid, followed by repeated washing with 300 ml of water. The carbon tetrachloride solution was dried over anhydrous magnesium sulfate.

To the carbon tetrachloride solution obtained, 8.2 g of azo-bis(isobutylonitrile) was added and, while refluxed at 78° C., 160 g of bromine in 40 ml carbon tetrachloride solution was added dropwise in an hour and reaction was continued until the color of bromine disappeared.

During the first and second stages of bromination reactions deposition of an insoluble matter was not observed in the carbon tetrachloride.

When the reaction was completed, the reaction solution was concentrated to dryness and dissolved in 550 ml of benzene. While the solution being refluxed under heating, 36 g of potassium hydroxide in 150 ml of methanol was added in drops in an hour and then reaction was continued for additional one hour. The reaction solution was cooled and separated potassium bromide was removed by filtration. Methanol was removed by distillation and washed 3 times with water. The benzene solution was concentrated and dropwise added into cold acetone (0° ~ −10° C.), to reprecipitate 152 g of condensed bromoacenaphthylene. Composition of the condensate corresponded to $(C_{12}H_{4.7}Br_{3.2})m$ and the yield was 75.1% from acenaphthene.

Melting point, elemental analysis, and the degree of condensation of the resulting condensate were as follows.

Melting point: 135°–140° C.

Elemental analysis: C, 35.6; H, 1.4; Br, 62.7%
Analysis by HPLC (GPC):
Mono- and dimer; 38%
Trimer; 41%
Tetra to octomer; 21%

The instrument and the conditions of measurement were as follows:
Instrument: High Performance Liquid Chromatograph, TSK HLC 802, manufactured by Toyo Soda Manufacturing Co., Ltd.
Column: 7.5 mm in diameter, 600 mm in length Packed with TSK GEL G1000H8 (Trade name, supplied by Toyo Soda Manufacturing Co., Ltd.)

EXAMPLE 2

A mixture of 77 g of acenaphthene and 3.3 g of aluminum chloride in 690 ml of carbon tetrachloride was kept at 30° C. To this, 320 g of bromine in 80 ml of carbon tetrachloride was added dropwise in 4 hours and the reaction was continued until the color of bromine disappeared. The same treatment as in Example 1 was followed, and then 8.2 g of azo-bis(isobutylonitrile) was added. While the mixture being refluxed at 78° C., 80 g of bromine in 20 ml of carbon tetrachloride was added dropwise in 0.5 hour and the reaction continued while the color of bromine remained. No separation of insoluble matters was observed in these bromination reactions. Subsequent reactions, same as in Example 1, gave 162 g of condensed bromoacenaphthylene. Composition of the condensate as determined by elemental analysis corresponded to $(C_{12}H_{4.7}Br_{3.2})m$ and the yield from acenaphthene was 80.1%.

Analysis of the condensate gave following values.
Melting point: 155°–160° C.
Elemental analysis(%): C, 36.5; H, 1.2; Br, 64.6
Analysis by HPLC (GPC):
Mono- and dimer; 30%
Trimer; 32%
Tetra to octomer; 38%

EXAMPLE 3

77 g of acenaphthene and 8.1 g of iron (III) chloride were added to 300 ml of carbon tetrachloride, and the mixture was heated to 77° C. To this solution, 360 g of bromine dissolved in 100 ml of carbon tetrachloride was added dropwise in 4 hours. Reaction was further continued until the color of bromine disappeared. When the reaction was completed, an insoluble matter amounting to 8.2 g was removed by filtration and the solution was washed with 300 ml of a 1N aqueous solution of hydrochloric acid followed by repeated washing with 300 ml of water. The solution was then concentrated to dryness, dissolved in 550 ml of benzene, heated to reflux, and 36 g of potassium hydroxide dissolved in 150 ml of methanol was added in drops in an hour. Reaction was continued for additional one hour.

After the reaction solution was cooled, separated potassium bromide was removed by filtration, methanol was distilled, washed 3 times with water, and the benzene solution was concentrated and dropwise added into cold acetone (0° ~ −10° C.), to obtain reprecipitate of 140 g of condensed bromoacenaphthylene. Elemental analysis showed that the composition of the condensate corresponded to $(C_{12}H_{4.4}Br_{2.7})m$ and the yield from acenaphthene was 76.8%.

Melting point, elemental analysis, and analytical value of the degree of condensation were a follows.
Melting point: 120°–133° C.,
Elemental analysis(%): C, 39.1; H, 1.2; Br, 59.4,
Analysis by HPLC (GPC):
Mono- and dimer; 27%
Trimer; 31%
Tetra to octomer; 42%

Instrument used for the high performance liquid chromatographic analysis and the condition of measurements are as follows:
Instrument: High Performance Chromatograph, TSK HLC 802, manufactured by Toyo Soda Manufacturing Co., Ltd.
Column: 7.5 mm in diameter and 600 mm in length packed with TSK GEL G1000H8 (Trade mark, Toyo Soda Manufacturing Co., Ltd.)

EXAMPLE 4

A mixture of 77 g of acenaphthene and 4.2 g of iron powder was added to 500 ml of ethylenedibromide and the mixture was heated to 120° C. To this mixture, 400 g of bromine was dropwise added in 5 hours, and the reaction was continued until the color of bromine disappeared.

At the completion of reaction, an insoluble matter 5.2 g formed in the reaction mixture was removed by filtration. The same treatment as in Example 3 and the dehydrobromination reaction were conducted, to obtain 155 g of condensed bromoacenaphthylene. Composition of the condensate as determined by elemental analysis corresponded to $(C_{12}H_{4.4}Br_{3.1})m$ and the yield from acenaphthene was 78.2%.

Melting point of the condensate obtained, elemental analysis and the degree of condensation were as follows.
Melting point: 125°–140° C.
Elemental analysis(%): C, 36.4; H, 1.1; Br, 62.1
Analysis by HPLC (GPC):
Monomer and dimer; 27%
Trimer; 28%
Tetra to octomer; 45%

REFERENCE EXAMPLE 1

To 700 ml of carbon tetrachloride were added 77 g of acenaphthene and 8.1 g of iron (III) chloride and the mixture was kept at 20° C. To this solution, 480 g of bromine dissolved in 120 g of carbon tetrachloride was dropwise added in 4 hours. When the addition was completed, the temperature of the solution was raised to 55° C. and reaction was continued till the color of bromine disappeared. Dark brown insoluble matter formed in the reaction mixture amounting to 80 g was removed by filtration. The solution was washed with hydrochloric acid and water successively and dehydrobromination reaction was conducted in the same manner as in Example 3, to obtain 140 g of condensed bromoacenaphthylene. Composition as determined by elemental analysis corresponded to $(C_{12}H_{3.4}Br_{4.2})m$ and the yield from acenaphthene was 57.9%.

Analysis showed that the insoluble matter separated was monomer of brominated acenaphthene containing 75% of bromine. The condensed bromoacenaphthylene thus obtained showed a melting point at 130°–142° C., a bromine content of 69%, and the degree of condensation was 37% of monomer and dimer, 43% of trimer and 20% of tetramer through octomer.

Followings are the embodiments of the purification process according to the present invention.

EXAMPLE 5

308 grams of acenaphthene and 32 g of iron (III) chloride were added to 2.8 liters of carbon tetrachloride and the temperature was maintained at 20° C. To this solution, 1.9 kg of bromine dissolved in 0.5 liter of carbon tetrachloride was added dropwise in 4 hours, then the temperature was elevated up to 55° C. Reaction continued until the color of bromine disappeared. Insoluble matter that formed in the reaction mixture was removed by filtration. The reaction solution was concentrated to dryness. The residue formed was dissolved in 2.2 liters of benzene. While the solution being heated to reflux, 144 g of potassium hydroxide dissolved in 0.6 liter of methanol was dropwise added in an hour. After the reaction solution was cooled, the formed potassium bromide salt was removed by filtration, methanol was distilled off, and the remaining solution was washed 3 times with water. The benzene solution was concentrated and droppingly added to cold acetone (0° ~ −10° C.), to reprecipitate 560 g of condensed bromoacenaphthylene. Analysis showed that the composition of the condensate corresponded to $(C_{12}H_{3.4}Br_{4.2})m$. Melting point was 128°–146° C. The degree of condensation as determined by gel permuation chromatography was 37% for mono- and dimer, 43% for trimer, and 20% for tetra through octomer.

250 grams of this condensate was dissolved in 1.3 liters of benzene, to make up a treating solution. On the other hand, 70 g of active alumina (neutral, activity I, and 70–230 mesh) was packed in an cylindrical column of 12 mm diameter. Elution was conducted at 20° C. with SV=10, and the column was washed with 100 ml of benzene. The obtained liquid was concentrated to a ¼ volume and then poured into cold acetone (0° ~ −10° C.), to obtain purified condensed bromoacenaphthylene, which was separated by filtration, and dried. This was kneaded with EPDM rubber together with other substances as shown in Table 1, using a roller. In this mixing, however, all the ingredients except dicumylperoxide (DCP) as as radical generator were kneaded homogeneously with a roller heated to 120° C. and then DCP was added to it at 45° C. This was further pressed under heating for 30 minutes with a hot presser at 160° C., to obtain a sheet of 2 mm thickness.

Examination was made on the adherence to the roller during the kneading and the breed formation on the surface of shaped sheets. On the other hand, tensile strength, elongation and water-proofness against hot steam of the sheets were estimated. Results are shown in Table 2, where remarkable improvements can be seen in various properties of products by using the condensed bromoacenaphthylene purified according to this invention.

EXAMPLE 6

50 gram of crude product of condensed bromoacenaphthylene prepared in Example 5 was dissolved in 500 ml of carbon tetrachloride, to which 20 g of magnesium silicate in powdery form was added, and the mixture was agitated at 20° C. for an hour. The reaction solution was filtered and then washed with 50 ml of carbon tetrachloride. The filtrate was concentrated and poured into cold acetone, to obtain 38 g of condensed bromoacenaphthylene by filtration followed by drying. This was kneaded, as in Example 5, with EPDM rubber, to make a sheet. Various properties estimated and shown in Table 2 proved satisfactory.

EXAMPLE 7

A liquid was prepared which consisted of the same components and each component being of the same quantity as those in Example 6. To the liquid, 5 g of active charcoal in powder form was added and agitated at 50° C. for 2 hours. Post-treatment as shown in Example 6 was applied, kneaded with EPDM rubber, and then shaped into a sheet. Thus, properties of purified condensed bromoacenaphthylene was provided with satisfactory properties which were acceptable for practical uses.

REFERENCE EXAMPLE 2

The crude condensed bromoacenaphthylene in Example 5 was used to be kneaded together with EPDM rubber, to form a sheet. Estimated properties, shown in Table 2, proved to be poor for practical uses.

TABLE 1

| Ingredients of EPDM composition | |
|---|---|
| Ingredient | Parts by weight |
| EPDM (Nippon Synthetic Rubber EP-21) | 100 |
| Stearic acid | 1 |
| Zinc white (ZnO) | 5 |
| Sulfur | 0.4 |
| Talc | 100 |
| Condensed bromcacenaphthylene | 45 |
| Antimony trioxide | 12 |
| Dicumylperoxide (DCP) | 3 |

TABLE 2

| | Effect of purification on various properties | | | |
|---|---|---|---|---|
| | Example | | | |
| Item of estimation | Example 5 | Example 6 | Example 7 | Reference Example 2 |
| Adherence on roller | No | No | No | Yes |
| Breed formation | No | No | No | Yes |
| Tensile strength, kb/cm² | 97.4 | 90.5 | 92.7 | 67.2 |
| Elongation, % | 609 | 561 | 581 | 167 |
| Swelling* in hot water (150° C., 24 hours), % | 108 | 106 | 108 | 113 |

*(Thickness after treatment)/(Thickness before treatment) × 100

What we claim:

1. A process for producing condensed bromoacenaphthylene having the general (I) or (II)

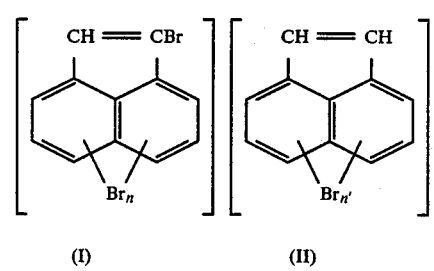

(I)   (II)

as elementary unit, wherein n and n' are integers ranging from 1 to 5, the bonding being made intermolecularly between a benzylic carbon of one acenaphthylene and an arylic carbon of another acenaphthlene, comprising:

(A) brominating and condensing acenaphthene with from 1 to 5 moles of bromine per mole of acenaphthene in a halogenated hydrocarbon solvent in the presence of an iron or aluminum catalyst;

(B) removing said catalyst from the bromination medium and then continuing the bromination reaction with bromine in the presence of added radical initiator; and (C) dehydrobrominating the product of step (B) to obtain said condensed bromoacenaphthylene product.

2. The process of claim 1, wherein the halogenated hydrocarbon solvent in step A is a member selected from the group consisting of carbon tetrachloride, chloroform, methylenechloride, ethylenedichloride, ethylenedibromide and chlorobenzene.

3. The process according to claim 1, wherein the amount of bromine added in step (B) ranges from 1 to 2 moles per unit mole of acenaphthene.

4. The process of claim 1, wherein said radical initiator is benzoyl peroxide, acetyl peroxide, lauroyl peroxide or azobis(isobutyronitrile).

5. The process of claim 1, wherein said iron or aluminum catalyst is present in the reaction medium of step (A) in an amount ranging from 0.1 to 50 mole per unit mole of acenaphthene.

6. The process of claim 5, wherein said catalyst is present in the reaction medium of step (A) in an amount ranging from 1 to 20 mole % per unit mole of acenaphthene.

7. The process of claim 1, wherein said dehydrobromination reaction of step (C) is conducted by the addition of a base in a solvent selected from the group consisting of carbon tetrachloride, ethylene dichloride, hexane, benzene, toluene and tetrahydrofuran.

8. The process of any one of claim 1 to 7, wherein said condensed bromoacenaphthylene product comprises a plurality of condensed materials of the formula:

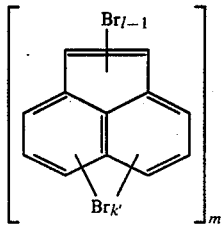

wherein m is a plurality of values ranging from 1 to 10, k' represents integers ranging from 1 to 5 and 1 is one or 2.

9. A process for producing condensed bromoacenaphthylene having the general formula (I) or (II)

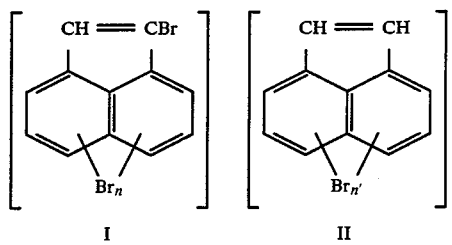

as elementary unit, wherein n and n' are integers ranging from 1 to 5, the bonding being made intermolecularly between a benzylic carbon of one acenaphthylene and an arylic carbon of another acenaphthylene, comprising:

(A) brominating and condensing acenaphthene with from 3 to 5 moles of bromine per mole of acenaphthene in a halogenated hydrocarbon solvent at a temperature not less than 60° C. in the presence of an iron catalyst;

(B) removing said iron catalyst and then continuing the bromination reaction with bromine in the presence of added radical intiator; and (C) dehydrobrominating the product of step (B) to obtain said condensed bromoacenaphthylene product.

10. The process of claim 9, wherein said halogenated hydrocarbon solvent in step (A) is a member selected from the group consisting of carbon tetrachloride, chloroform, dichloroethylene, dibromoethylene, chlorobenzene, bromobenzene and dichlorobenzene.

11. The process of claim 9, wherein said iron catalyst is an iron halogenide, an iron salt, an iron oxide or iron powder and is utilized in the reaction of step (A) in an amount ranging from 0.001 to 0.5 mole per unit mole of acenaphthene.

12. The process of claim 11, wherein said iron halogenide is iron (II) chloride or iron (III) bromide, said iron salt is iron (III) phosphate and said iron oxide is iron (III) oxide.

13. A process for producing condensed bromoacenaphthylene having the general formula [I] or [II]

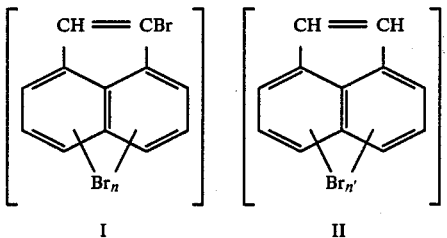

as elementary unit, wherein n and n' are integers ranging from 1 to 5, the bonding being made intermolecularly between a benzylic carbon of one acenaphthylene and an arylic carbon of another acenaphthylene, comprising:

(a) brominatng and condensing acenaphthene in a halogenated hydrocarbon solvent at a temperature not less than 60° C. with at least 3 moles of bromine per mole of acenaphthene in the presence of an iron catalyst; and (b) dehydrobrominating the brominated and condensed product of step (A) thereby obtaining said condensed bromoacenaphthylene product.

14. The process according to claim 13, wherein said bromination and condensation reaction is carried out at 70° to 170° C.

15. The process according to claim 13, wherein the amount of bromine present ranges from 3 to 6 moles per mole of acenaphthene.

16. The process according to claim 13, in which the halogenated hydrocarbon solvent is a member selected from the group consisting of carbon tetrachloride, chloroform, dichlooethylene, dibromoethylene, chlorobenzene, bromobenzene and dichlorobenzene.

17. The process according to claim 13, in which the iron catalyst is a member selected from the group consisting of iron halogenides, iron salts, iron oxide or iron powder and is present in the reaction of step (A) in an amount ranging from 0.001 to 0.5 mole per mole of acenaphthene.

18. The process according to claim 17, wherein said iron halogenide is iron (II) chloride, (III) chloride or iron (III) bromide, said iron salt is iron (III) phosphate and said iron oxide is iron (III) oxide.

19. The process of any one of claims 13 to 18, wherein said condensed bromoacenaphthylene product comprises a plurality of condensed materials of formula:

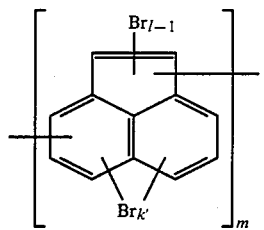

wherein m is a plurality of values ranging from 2 to 10, k' is an integer of 1 to 5 and l is one or two.

* * * * *